(12) United States Patent
Bentley et al.

(10) Patent No.: US 6,583,134 B2
(45) Date of Patent: Jun. 24, 2003

(54) AZA- INDOLYL DERIVATIVES FOR TREATING OBESITY

(75) Inventors: Jonathan Mark Bentley, Reading (GB); Paul Hebeisen, Basel (CH); Sven Taylor, Riedisheim (FR)

(73) Assignees: Hoffman-La Roche Inc., Nutley, NJ (US); Vernalis Research Limited, Winnersh (GB)

( * ) Notice: Subject to any disclaimer, the term of this patent is extended or adjusted under 35 U.S.C. 154(b) by 0 days.

(21) Appl. No.: 09/794,491

(22) Filed: Feb. 27, 2001

(65) Prior Publication Data

US 2001/0025039 A1 Sep. 27, 2001

(30) Foreign Application Priority Data

Mar. 6, 2000 (EP) ............................................ 00301814

(51) Int. Cl.⁷ ...................... A61K 31/55; C07D 223/14; C07D 487/00; C07D 491/00; C07D 515/00
(52) U.S. Cl. .................. 514/214.02; 514/248; 514/250; 514/267; 514/292; 514/411; 540/576; 540/579; 540/580; 540/586; 544/234; 544/250; 546/81; 546/84; 546/94
(58) Field of Search ............................ 514/214.02, 248, 514/250, 267, 411, 292; 540/576, 579, 580, 586; 544/234, 250; 546/81, 84, 94

(56) References Cited

U.S. PATENT DOCUMENTS

| | | | |
|---|---|---|---|
| 4,598,089 A | 7/1986 | Hadvary et al. | 514/449 |
| 4,931,463 A | 6/1990 | Barbier et al. | 514/422 |
| 4,983,746 A | 1/1991 | Barbier et al. | 549/328 |
| 5,245,056 A | 9/1993 | Karpf et al. | 549/510 |
| 5,494,928 A | 2/1996 | Bös | 548/469 |
| 5,512,564 A * | 4/1996 | Zilch et al. | 514/224.5 |
| 5,639,779 A | 6/1997 | Wythes et al. | 514/414 |
| 6,004,996 A | 12/1999 | Shah et al. | 514/449 |
| 6,495,543 B1 * | 12/2002 | Guillaumet et al. | 514/217.02 |

FOREIGN PATENT DOCUMENTS

| | | |
|---|---|---|
| CA | 2132887 | 4/1995 |
| CA | 2153937 | 2/1996 |
| EP | 167 901 | 1/1986 |
| EP | 185 359 | 6/1986 |
| EP | 189 577 | 8/1986 |
| EP | 252 643 | 1/1988 |
| EP | 279 125 | 8/1988 |
| EP | 443 449 | 8/1991 |
| EP | 620 222 | 10/1994 |
| EP | 655 440 | 5/1995 |
| WO | WO 98/30548 | 7/1998 |
| WO | WO 99/34786 | 7/1999 |
| WO | WO 00/09122 | 2/2000 |
| WO | WO 00/09123 | 2/2000 |

OTHER PUBLICATIONS

Bös et al., J. Med. Chem., vol. 40, pp. 2762–2769 (1997).
Parker, "Obesity: Trends and Treatments", Scrip Reports, PJB Publications Limited, (1996).
Kennett et al., Psychopharmacology, 96, pp. 93–100 (1988).
Kennett et al., Eur. J. Pharmacol., 141, pp. 429–435 (1987).
Kitchener et al., Psychopharmacology, 113, pp. 369–377 (1994).
Walsh et al., Psychopharmacology, 116, pp. 120–122 (1994).
Sargeant et al., Psychopharmacology, 133, pp. 309–312 (1997).

* cited by examiner

Primary Examiner—Richard L. Raymond
Assistant Examiner—Tamthom N. Truong
(74) Attorney, Agent, or Firm—George W. Johnston; Dennis P. Tramaloni; Eileen M. Ebel

(57) ABSTRACT

Novel compounds of formula (I):

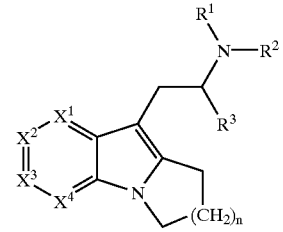

wherein $X^1$, $X^2$, $X^3$ and $X^4$, n, $R^1$, $R^2$ and $R^3$ are defined in the specification, and pharmaceutically acceptable salts and prodrugs of the compounds of formula (I) have therapeutic uses. These compounds are useful for the treatment of disorders of the central nervous system; damage to the central nervous system; cardiovascular disorders; gastrointestinal disorders; diabetes insipidus, and sleep apnea. They are particularly useful for the treatment of obesity.

31 Claims, No Drawings

AZA-INDOLYL DERIVATIVES FOR TREATING OBESITY

FIELD OF THE INVENTION

The present invention relates to new aza-indolyl derivatives, to processes and intermediates for their preparation, to pharmaceutical compositions containing them and to their medicinal use. The active compounds of the present invention are useful in treating obesity and other disorders.

BACKGROUND OF THE INVENTION

It has been recognized that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI) which is calculated by dividing body weight (kg) by height squared (m²). Thus, the units of BMI are kg/m² and it is possible to calculate the BMI range associated with minimum mortality in each decade of life. Overweight is defined as a BMI in the range 25–30 kg/m², and obesity as a BMI greater than 30 kg/m². There are problems with this definition in that it does not take into account the proportion of body mass that is muscle in relation to fat (adipose tissue). To account for this, obesity can also be defined on the basis of body fat content: greater than 25% and 30% in males and females, respectively. Using BMI and/or other conventional diagnosis tools, prescribing doctors are well able to determine which of their patients are in need of treatment for obesity.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective $5\text{-HT}_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, *Psychopharmacol.*, 1988, 96, 93–100; G. A. Kennett, C. T. Dourish and G. Curzon, *Eur. J. Pharmacol.*, 1987, 141, 429–435) and to accelerate the appearance of the behavioural satiety sequence (S. J. Kitchener and C. T. Dourish, *Psychopharmacol.*, 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., *Psychopharmacol.*, 1994, 116, 120–122) and decreased the appetite and body weight of obese male and female subjects during subchronic treatment for a 14 day period (P. A. Sargeant et al., *Psychopharmacol.*, 1997, 133, 309–312). The anorectic action of mCPP is absent in $5\text{-HT}_{2C}$ receptor knockout mutant mice (L. H. Tecott et al., *Nature*, 1995, 374, 542–546) and is antagonised by the $5\text{-HT}_{2C}$ receptor antagonist SB-242084 in rats (G. A. Kennett et al., *Neuropharmacol.*, 1997, 36, 609–620). It seems therefore that mCPP decreases food intake via an agonist action at the $5\text{-HT}_{2C}$ receptor.

Other compounds which have been proposed as $5\text{-HT}_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to $5\text{-HT}_{2C}$ receptors and may be used in the treatment of obesity. WO-A-98/30548 discloses aminoalkylindazole compounds as $5\text{-HT}_{2C}$ agonists for the treatment of CNS diseases and appetite regulation disorders. 2-(2,3-Dihydro-1H-pyrrolo[1,2-a]indol-9-yl)ethylamine is disclosed in *J.Med.Chem.*, 1965, 8, 700. The preparation of pyrido[1,2-a]indoles for the treatment of cerebrovascular disorders is disclosed in EP-A-0252643 and EP-A-0167901. The preparation of 10-[(acylamino)ethyl]tetrahydropyrido[1,2-a]indoles as anti-ischemic agents is disclosed in EP-A-0279125.

It is an object of this invention to provide selective, directly acting $5\text{HT}_2$ receptor ligands for use in therapy and particularly for use as anti-obesity agents. It is a further object of this invention to provide directly acting ligands selective for $5\text{-HT}_{2B}$ and/or $5\text{-HT}_{2C}$ receptors, for use in therapy and particularly for use as anti-obesity agents. It is a further object of this invention to provide selective, directly acting $5\text{-HT}_{2C}$ receptor ligands, preferably $5\text{-HT}_{2C}$ receptor agonists, for use in therapy and particularly for use as anti-obesity agents.

SUMMARY OF THE INVENTION

According to the present invention there is provided a chemical compound of formula (I):

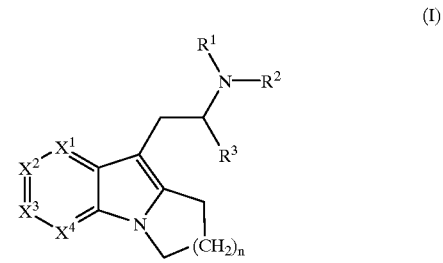

(I)

wherein
n is 1, 2 or 3;
$X^1$ is nitrogen or $CR^4$; $X^2$ is nitrogen or $CR^5$; $X^3$ is nitrogen or $CR^6$; $X^4$ is nitrogen or $CR^7$; wherein one or two of $X^1$, $X^2$, $X^3$ and $X^4$ are nitrogen;
$R^1$, $R^2$ and $R^3$ are independently selected from hydrogen and alkyl;

$R^4$, $R^5$, $R^6$ and $R^7$ are independently selected from hydrogen, halogen, hydroxy, alkyl, aryl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, and wherein a carbon ring atom next to a nitrogen is not substituted by halogen;

and pharmaceutically acceptable salts and prodrugs thereof. Preferred are the compounds according to formula (I) and salts thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl) or butyl (n-butyl, isobutyl or tertiary-butyl), more preferably methyl.

As used herein, the term "lower alkyl" means methyl, ethyl, propyl (n-propyl or isopropyl) or butyl (n-butyl, isobutyl or tertiary-butyl). Preferably, these lower alkyl groups are unsubstituted.

As used herein, the term "aryl" means an aromatic group, such as phenyl or naphthyl, or a heteroaromatic group containing one or more, preferably one, heteroatom, such as pyridyl, pyrrolyl, furanyl and thienyl.

The alkyl and aryl groups may be substituted or unsubstituted. Where substituted, there will generally be 1 to 3 substituents present, preferably 1 substituent. Substituents may include:

carbon-containing groups such as
    alkyl,
    aryl,
    arylalkyl (e.g. substituted and unsubstituted phenyl, substituted and unsubstituted benzyl);
halogen atoms and halogen-containing groups such as
    haloalkyl (e.g. trifluoromethyl);
oxygen-containing groups such as
    alcohols (e.g. hydroxy, hydroxyalkyl, aryl(hydroxy)alkyl),
    ethers (e.g. alkoxy, aryloxy, alkoxyalkyl, aryloxyalkyl),
    aldehydes (e.g. carboxaldehyde),
    ketones (e.g. alkylcarbonyl, alkylcarbonylalkyl, arylcarbonyl, arylalkylcarbonyl, arylcarbonylalkyl),
    acids (e.g. carboxy, carboxyalkyl),
    acid derivatives such as esters (e.g. alkoxycarbonyl, alkoxycarbonylalkyl, alkylcarbonyloxy, alkylcarbonyloxyalkyl),
    amides (e.g. aminocarbonyl, mono- or di-alkylaminocarbonyl, aminocarbonylalkyl, mono- or di-alkylaminocarbonylalkyl, arylaminocarbonyl),
    carbamates (e.g. alkoxycarbonylamino, aryloxycarbonylamino, aminocarbonyloxy, mono- or di-alkylaminocarbonyloxy, arylaminocarbonyloxy)
    and ureas (e.g. mono- or di-alkylaminocarbonylamino or arylaminocarbonylamino);
nitrogen-containing groups such as
    amines (e.g. amino, mono- or di-alkylamino, aminoalkyl, mono- or di-alkylaminoalkyl),
    azides,
    nitriles (e.g. cyano, cyanoalkyl),
    nitro;
sulfur-containing groups such as
    thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);
and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthyridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O— and "alkoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical.

As used herein the term "prodrug" means any pharmaceutically acceptable prodrug of the compound of formula (I).

As used herein, the term "pharmaceutically acceptable salt" or "salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

The term "lipase inhibitor" refers to compounds that are capable of inhibiting the action of lipases, for example gastric and pancreatic lipases. For example orlistat and lipstatin as described in U.S. Pat. No. 4,598,089 are potent inhibitors of lipases. Lipstatin is a natural product of microbial origin, and orlistat is the result of a hydrogenation of lipstatin. Other lipase inhibitors include a class of compounds commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterised in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilising agents, wetting agents, emulsifying agents, sweetening agents, colouring agents, flavouring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

In a preferred embodiment the present invention refers to compounds as defined above wherein in case two of $X^1$, $X^2$, $X^3$ and $X^4$ are nitrogen these nitrogen atoms are in meta or para position to each other.

In a preferred embodiment the present invention refers to compounds as defined above wherein $X^1$ is nitrogen, $X^2$ is $CR^5$, $X^3$ is $CR^6$, and $X^4$ is $CR^7$.

In a further preferred embodiment the present invention refers to compounds as defined above wherein $X^1$ is $CR^4$; $X^2$ is nitrogen; $X^3$ is $CR^6$ and $X^4$ is $CR^7$.

In a further preferred embodiment the present invention refers to compounds as defined above wherein $X^1$ is $CR^4$, $X^2$ is $CR^5$; $X^3$ is nitrogen and $X^4$ is $CR^7$.

In a further preferred embodiment the present invention refers to compounds as defined above wherein $X^1$ is $CR^4$, $X^2$ is $CR^5$; $X^3$ is $CR^6$ and $X^4$ is nitrogen.

In a further preferred embodiment the present invention refers to compounds as defined above wherein $X^1$ is nitrogen, $X^2$ is $CR^5$, $X^3$ is nitrogen and $X^4$ is $CR^7$.

In a further preferred embodiment the present invention refers to compounds as defined above wherein $X^1$ is $CR^4$, $X^2$ is nitrogen, $X^3$ is $CR^6$ and $X^4$ is nitrogen.

In a further preferred embodiment the present invention refers to compounds as defined above wherein $X^1$ is nitrogen, $X^2$ is $CR^5$, $X^3$ is $CR^6$ and $X^4$ is nitrogen.

In a preferred embodiment, the compounds of formula (I) are selected from compounds in which n is 1.

Preferably, the compounds of formula (I) are selected from compounds in which $R^1$ is the same as $R^2$. Preferably, $R^1$ and $R^2$ are both hydrogen. In a preferred embodiment of the invention, $R^1$ is hydrogen and $R^2$ is alkyl (preferably lower alkyl and more preferably methyl) optionally substituted by an aryl (preferably a substituted or unsubstituted phenyl or thienyl group) or by a cycloalkyl group (preferably saturated and preferably selected from a $C_3$, $C_4$, $C_5$, $C_6$ and $C_7$ cycloalkyl group).

Preferably, the compounds of formula (I) are selected from compounds in which $R^3$ is lower alkyl, preferably methyl or ethyl, preferably methyl.

$R^4$ to $R^7$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino.

In an embodiment of the invention, $R^4$ to $R^7$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, alkylsulfoxyl and alkylsulfonyl.

It is preferred that $R^4$ is selected from hydrogen and halogen, preferably hydrogen.

It is preferred that $R^5$ is selected from a substituent group other than hydrogen, and preferably from halogen, alkyl, alkoxy, alkylthio, alkylsulfonyl, monoalkylamino and dialkylamino, and more preferably from halogen (preferably fluoro, chloro and bromo), alkyl (preferably lower alkyl and preferably trifluoromethyl), alkoxy (preferably lower alkoxy) and alkylthio (preferably lower alkylthio).

It is preferred that $R^6$ is selected from halogen (preferably fluoro and chloro) and hydrogen. In an embodiment of the invention, $R^6$ is a substituent group other than hydrogen.

In an embodiment of the invention, two or three of $R^4$, $R^5$, $R^6$ and $R^7$, preferably two or three of $R^4$, $R^6$ and $R^7$ are hydrogen.

In a most preferred embodiment of the invention, one of $X^1$, $X^2$, $X^3$ and $X^4$ is nitrogen and the rest are CH; $R^1$, $R^2$ and $R^3$ are H or lower alkyl and n is 1 or 2. Compounds according to this most preferred embodiment include: (R,S)-2-(2,3-dihydro-1H-3a,6-diaza-cyclopenta[a]inden-8-yl)-1-methyl-ethylamine; (R,S)-2-(2,3-dihydro-1 H-3a,4-diaza-cyclopenta[a]inden-8-yl)-1-methyl-ethylamine; (R,S)-2-(2, 3-Dihydro-1H-3a,5-diaza-cyclopenta[a]inden-8-yl)-1-methyl-ethylamine; 2-(2,3-dihydro-1H-3a,6-diaza-cyclopenta[a]inden-8-yl)-ethylamine and isolated enantiomers thereof.

Where the compounds of formula (I) are in salt form, the fumarate salts are preferred.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis.

According to a further aspect of the invention, there is provided a compound of formula (I) for use in therapy.

The compounds of formula (I) may be used in the treatment (including prophylactic treatment) of disorders associated with 5-HT$_2$ receptor function. The compounds may act as receptor agonists or antagonists. Both agonists and antagonists are useful in treating disorders associated with 5-HT$_2$ receptor function, depending on whether the disorder is associated with insufficient or excessive 5-HT$_2$ receptor function. Whether any particular compound of formula (I) is an agonist or antagonist can be determined by the "Functional activity" assay taught in the Experimental section below. Preferably, the compounds may be used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required, such as obesity.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment (including prophylaxis) of the above-mentioned disorders. In a preferred embodiment, there is provided use of a compound of formula (I) in the manufacture of a medicament for the treatment (including prophylaxis) of obesity. The term obesity includes eating disorders.

According to a further aspect of the invention, there is provided a method of treatment (including prophylaxis) of a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I), especially a method comprising reduction and/or reductive alkylation of a compound of formula (VI)

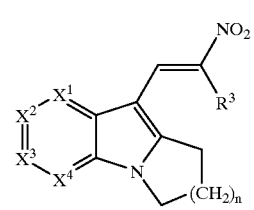

(VI)

wherein $X^1$, $X^2$, $X^3$, $X^4$, $R^3$ and n are as defined above.

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom (C*)" means a carbon atom with four different substituents. According to the Cahn-Ingold-Prelog-Convention the asymmetric carbon atom can be of the "R" or "S" configuration.

Preferred are chiral compounds of formula (I), wherein $R^1$ to $R^3$, $X^1$ to $X^4$ and n are defined as before. Particularly preferred are compounds according to formula (Ib)

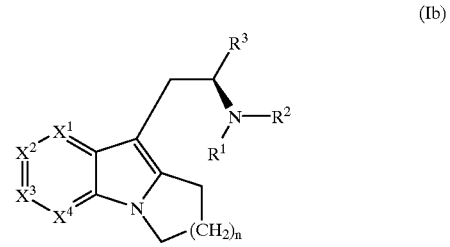

(Ib)

wherein $R^1$ to $R^3$, $X^1$ to $X^4$ and n are defined as before. Formula (Ib) means that the asymmetric carbon atom C*

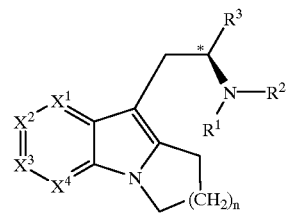

is of the R configuration.

A further particularly preferred aspect of the present invention are compounds according to formula (Ia)

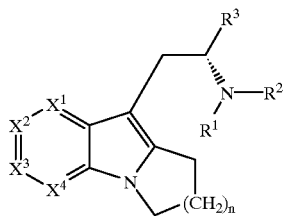

(Ia)

wherein $R^1$ to $R^3$, $X^1$ to $X^4$ and n are defined as before. Formula (Ia) means that the asymmetric carbon atom C*

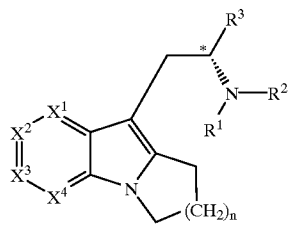

is of the S configuration.

Likewise preferred are compounds of formula I, wherein $R^3$ is hydrogen.

Particularly preferred are compounds of formula I selected from the following compounds:

- (S)-2-(2,3-dihydro-1H-3a,5-diaza-cyclopenta[a]inden-8-yl)-1-methyl-ethylamine;
- (R)-2-(2,3-dihydro-1H-3a,5-diaza-cyclopenta[a]inden-8-yl)-1-methyl-ethylamine;
- (S)-2-(2,3-dihydro-1H-3a,6-diaza-cyclopenta[a]inden-8-yl)-1-methyl-ethylamine;
- (R)-2-(2,3-dihydro-1H-3a,6-diaza-cyclopenta[a]inden-8-yl)-1-methyl-ethylamine;
- and 2-(2,3-dihydro-1H-3a,6-diaza-cyclopenta[a]inden-8-yl)-ethylamine.

Another preferred aspect of the invention is a method of treatment of obesity in a human in need of such treatment which comprises administration to the human a therapeutically effective amount of a compound of the present invention and a therapeutically effective amount of a lipase inhibitor. Particularly preferred is this method of treatment, wherein the lipase inhibitor is orlistat.

Further preferred is the use of a compound of the present invention in the manufacture of a medicament for the treatment and prevention of obesity in a patient who is also receiving treatment with a lipase inhibitor. Particularly preferred is this use, wherein the lipase inhibitor is orlistat.

Another preferred aspect is the pharmaceutical composition, as above, further comprising a therapeutically effective amount of a lipase inhibitor. Particularly preferred is this pharmaceutical composition, wherein the lipase inhibitor is orlistat.

Compounds of the invention may be prepared according to Reaction Scheme 1 below. $R^1$ to $R_7$ are as previously defined.

Compounds of formula (II) may be prepared by reaction of the corresponding protected amine with iodine ($I_2$, nBuLi, TMEDA) and deprotection of the amino group. The corresponding amines are available commercially or has been described in the literature for many combinations of $X^1$, $X^2$, $X^3$ and $X^4$, such as amino-pyridino, amino-pyrimidino and amino-pyrazine derivatives, and the introduction of an amino-protecting group can be performed by conventional methods. Some starting compounds in which one or more X is CR where R is not hydrogen are also commercially available, e.g. with methoxy or halogen substituents. Conversion of such an R group into another desired substituent, for instance into hydroxy, can also be performed by conventional methods. All possible starting reactants for Scheme I meeting the definitions of $X^1$, $X^2$, $X^3$ and $X^4$ from formula (I) can be prepared by conventional methods from commercially available starting materials or compounds described in the literature.

Compounds of formula (II) may be reacted with compounds of formula (III) under palladium catalysed conditions to give compounds of formula (IV). Alkynes such as compounds of the formula (III) are well-described in the literature and the compounds of formula (III) can be derived from commercially available materials by conventional methods. The carboxaldehyde (V) may be obtained by reaction of compound (IV) with e.g. the Vilsmeier reagent prepared from DMF and phosphorus oxychloride under standard conditions. The nitroalkene (VI) may be obtained by reaction of compound (V) with a nitroalkane. Compounds of formula (I) can be formed in the reaction of the nitroalkene (VI) with a reducing agent such as lithium aluminium hydride in an ethereal solvent.

Reaction Scheme 1

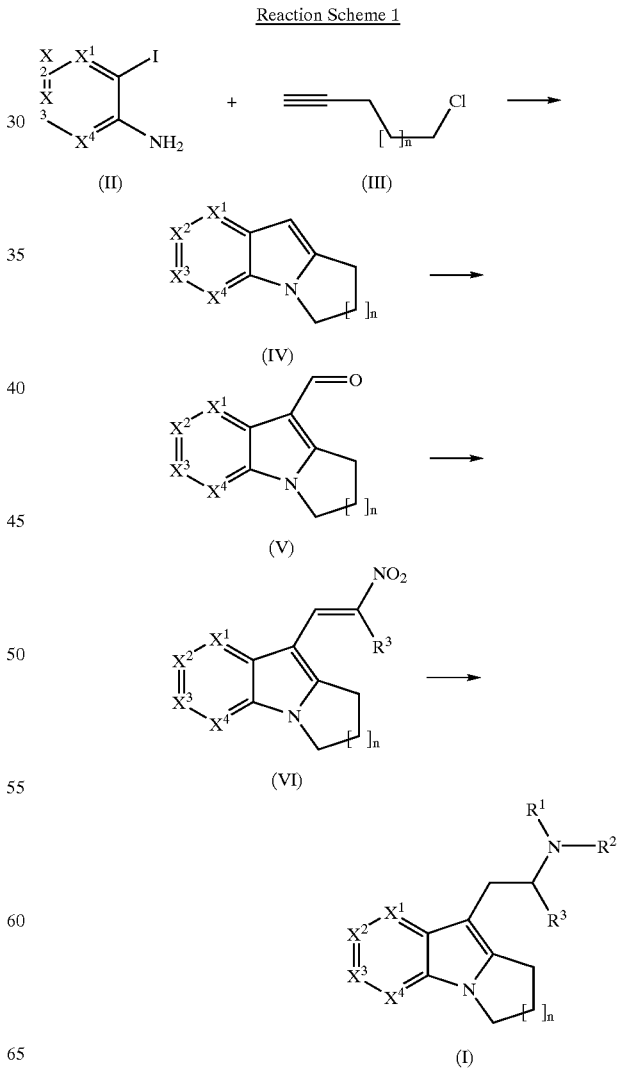

The compounds of formula (I) ($R^1$ and/or $R^2$=alkyl) may be prepared from compounds of formula (I) ($R^1$=$R^1$=H) by standard methods such as reductive alkylation with an appropriate aldehyde or ketone in the presence of a reducing agent such as sodium triacetoxcyborohydride, formic acid or sodium cyanoborohydride.

According to a further aspect of the invention there is provided a method of preparing compounds of formula (I), especially in enantiomerically pure form shown in formula (Ic). See Scheme 2. The intermediate (IV) is halogenated, perferably brominated or iodinated with suitable halogenating reagents agents (e.g. bromine or N-Iodosuccinimide in an inert solvent e.g. dimethylformamide or acetonitrile) to yield an intermediate of formula (VII). This intermediate (VII) is treated with an agent effecting halogen-metal exchange, preferably halogen-lithium exchange (e.g. with butyl-lithium in an inert solvent e.g. THF) and treated with the novel chiral Sulfamidate A to yield an intermediate of formula (VIII). This latter intermediate (VIII) is transformed to a compound of formula (I) by methods known in the art, particularly by acid mediated cleavage of the BOC (meaning tert-butlyoxycarbonyl) protecting group. Particularly preferred acids are trifluoroacetic acid or mixtures of trifluoroacetic acid in inert solvents such as dichloromethane and solutions of hydrochloric acid in inert solvents such as ethyl acetate, dioxane or diethyl ether. The stereochemistry, as indicated by the star (*), present in the chiral Sulfamidates A is without loss of integrity transferred onto the intermediates (VIII) and compounds (I).

in the presence of suitable catalysts such as rutheniumdioxide hydrate. The stereochemistry, as indicated by the star (*), present in the BOC protected alpha amino alcohols is without loss of integrity transferred onto the intermediates B and compounds A.

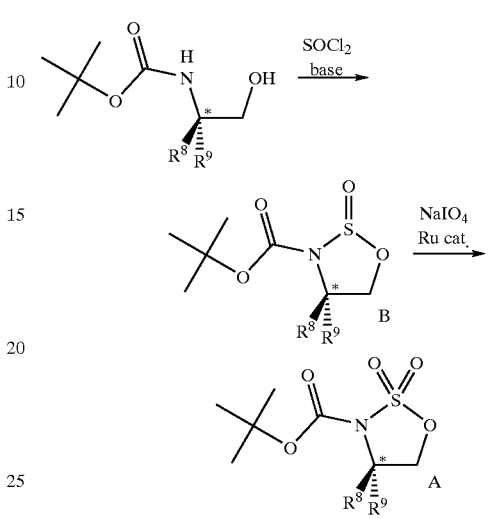

Scheme 3

$R^8$ is H and $R^9$ is alkyl, or $R^8$ is alkyl and $R^9$ is H

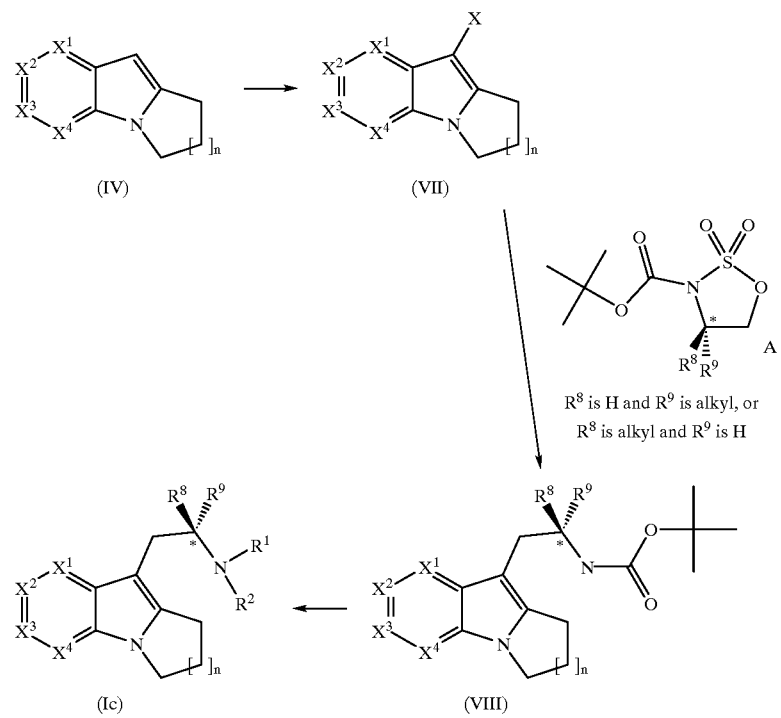

scheme 2

$R^8$ is H and $R^9$ is alkyl, or
$R^8$ is alkyl and $R^9$ is H

The novel sulfamidates of type A are conveniently obtained from commercially available BOC protected alpha amino alcohols, in particular BOC-glycinol, BOC-D-alalinol and BOC-L-alalinol, by first reacting with thionylchloride in an inert solvent such as tetrahydrofurane dichloromethane or ethyl acetate in the presence of a suitable base such as n-butyl lithium, triethylamine, imidazole or pyridine and the like and oxidizing the intermediate Sulfamidite B with suitable oxidizing agents such as sodium metaperiodate If, in any of the processes mentioned herein, the substituent group $R^4$, $R^5$, $R^6$ or $R^7$ is other than the one required, the substituent group may be converted to the desired substituent by known methods. The substituents $R^4$, $R^5$, $R^6$ or $R^7$ may also need protecting against the conditions under which the reaction is carried out. In such a case, the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

EXPERIMENTAL

Assay Procedures
Binding to Serotonin Receptors

The binding of compounds of formula (I) to serotonin receptors was determined in vitro by standard methods. The preparations were investigated in accordance with the assays given hereinafter.

Method (a): For the binding to the $5\text{-HT}_{2C}$ receptor the $5\text{-HT}_{2C}$ receptors were radiolabeled with $[^3H]$-5-HT. The affinity of the compounds for $5\text{-HT}_{2C}$ receptors in a CHO cell line was determined according to the procedure of D. Hoyer, G. Engel and H. O. Kalkman, *European J. Pharmacol.*, 1985, 118, 13–23.

Method (b): For the binding to the $5\text{-HT}_{2B}$ receptor the $5\text{-HT}_{2B}$ receptors were radiolabeled with $[^3H]$-5-HT. The affinity of the compounds for human $5\text{-HT}_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the $5\text{-HT}_{2A}$ receptor the $5\text{-HT}_{2A}$ receptors were radiolabeled with $[^{125}I]$-DOI. The affinity of the compounds for $5\text{-HT}_{2A}$ receptors in a CHO cell line was determined according to the procedure of D. J. McKenna and S. J. Peroutka, *J. Neurosci.*, 1989, 9, 3482–90.

Functional Activity

The functional activity of compounds of formula (I) was assayed using a Fluorimetric Imaging Plate reader (FLIPR). CHO cells expressing the human $5\text{-HT}_{2C}$ or human $5\text{-HT}_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 $\mu L$/well of assay buffer (Hanks balanced salt solution containing 20 mM Hepes and 2.5 mM probenecid). The drug (dissolved in 50 $\mu L$ of the assay buffer) was added at a rate of 70 $\mu L$/sec to each well of the FLIPR 96 well plate during fluorescence measurements. The measurements were taken at 1 sec intervals and the maximum fluorescent signal was measured (approx 10–15 secs after drug addition) and compared with the response produced by 10 $\mu M$ 5-HT (defined as 100%) to which it was expressed as a percentage response (relative efficacy). Dose response curves were constructed using Graphpad Prism (Graph Software Inc.).

The compounds of formula (I) have activity at the h5-HT2c receptor in the range of 10,000 to 0.1 nM.

SYNTHESIS EXAMPLES

Example 1

(R,S)-2-(2,3-Dihydro-1H-3a,6-diaza-cyclopenta[a]inden-8-yl)-1-methylethylamine dihydrochloride

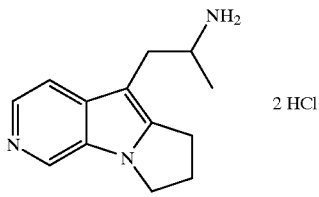

2 HCl

The compound was prepared according to methods known in the art: Xu, Lianhong; Lewis, Iestyn R.; Davidsen, Steven K.; Summers, James B. Tetrahedron Lett. (1998), 39(29), 5159–5162, for synthetic procedures for the preparation of 2-substituted 5-azaindoles; synthesis and cyclization reactions of acetylenic aminopyridines); Collini M D, Ellingboe J W, Tetrahedron Lett 38(46),7963–7966(1997, for Pd catalysed coupling of acetylenes to o-Iodoanilines); Iritani, K.; Matsubara, S.; Utimoto, K.; Tetrahedron Lett 1988, 29 (15), 1799. (1988, for Pd catalysed cyclisation of o-amino phenylacetylenes to indoles); Chen H G, Hoechstetter C, Knochel P, Tetrahedron Lett 30(36),4795–4798 (1989, for cyclisation of 2-(3-chloropropyl) indoles to 1H-pyrrolo[1,2-a]indoles).

2,3-Dihydro-1H-3a,6-diaza-cyclopenta[a]indene

To a solution of 4-Amino-3-iodopyridine (2.2 g, 10.00 mMol) in acetonitrile (25 ml), was added dropwise trifluoroacetic anhydride (2.53 g, 1.674 ml) at 0° C. followed by addition of potassium carbonate (4.14 g, 30 mMol). The mixture was stirred at room temperature for 10 min. To the resulting suspension was added bis(triphenylphosphine)-palladium(II)chloride (0.175 g, 0.25 mMol), copper(I)iodide (0.095 g, 0.50 mMol) and 5-chloro-1-pentyne (1.23 g, 12.00 mMol) and the mixture was heated to reflux under argon for 3 h. The mixture was cooled to room temperature and partitioned between water and ethyl acetate. The phases were separated. The organic phase was extracted with water at pH 1.00. The acidic aqueous phase was mixed with dichloromethane and the pH was raised to 10 by addition of 2N NaOH. The phases were separated and the organic phase was dried over sodium sulfate. The solvent was evaporated and the residue was taken up in acetonitrile (20 ml). To the brownish solution was added sodium iodide (3.00 g, 20 mMol) and sodium hydride (ca 55% 0.873 g, 20 mMol) and the mixture was stirred at room temperature for 2 h. The mixture was poured onto ice and partitioned between water and ethyl acetate (100 ml water 100 ml ethyl acetate). The phases were separated. The organic phase was extracted with water at pH 1.00 (5×50 ml). The combined acidic aqueous phases were mixed with dichloromethane (100 ml) and the pH was raised to 10 by addition of 2N NaOH. The phases were separated and the organic phase was dried over sodium sulfate. The solvent was evaporated and the title compound (0.81 g, 51% of theory) was obtained as a brownish solid. For analytical purposes a sample was recrystallised from t-butylmethylether to afford light brown crystals melting at 95–96° C.; Found C, 75.93; H. 6.32; N,17.80%. $C_{10}H_{10}N_2$ requires: C, 75.92; H, 6.37; N, 17.71%

2,3-Dihydro-1H-3a,6-diaza-cyclopenta[a]indene-8-carbaldehyde

To dimethylformamide (0.3 ml) was added phosphorus oxychloride (0.33 ml) dropwise at 0° C. The mixture was allowed to stir for 10 min at room temperature. A solution of 2,3-dihydro-1H-3a,6-diaza-cyclopenta[a]indene (0.10 g 0.63 mMol) in 0.1 ml dimethylformamide was added and the mixture was stirred at room temperature for 3 h. The reaction was quenched with ice (ca 5 g) and the pH was adjusted to 9 by addition of 28% sodium hydroxide. The mixture was heated to reflux for 10 min. cooled to room temperature and extracted with ethyl acetate(3×5 ml) The combined organic extracts were dried with sodium sulfate and evaporated to dryness to yield the title compound (0.115 g, 97% Th). For analytical purposes a sample was recrystallised from ethyl acetate to afford slightly yellow crystals. mp 150–151° C. Found C, 70.94; H, 5.56; N, 14.97%; $C_{11}H_{10}N_2O$ requires C, 70.95; H, 5.41; N. 15.04%

8-(2-Nitro-propenyl)-2,3-dihydro-1H-3a,6-diaza-cyclopenta[a]indene

To a solution of 2,3-dihydro-1H-3a,6-diaza-cyclopenta[a]indene-8-carbaldehyde (0.30 g 1.6 mMol) in nitroethane (3.00 ml) was added ammonium acetate (0.30 g 3.9 mMol) and the mixture was heated to 100° C. for 4 h with stirring under argon. The mixture was cooled to room temperature and purified by chromatography on silicagel gel (ca 30 g) eluting first with ethyl acetate (ca 100 ml) then with a mixture of ethyl acetate (9 parts) and methanol (1 part). The product fraction were combined, concentrated and the residue was recrystallised from ethyl acetate to yield the title compound (0.30 g, 77%) as yellow crystals. mp 141–142° C. Found C, 64.05; H, 5.51; N, 17.14%; $C_{13}H_{13}N_3O_2$ requires C, 64.19; H, 5.39; N, 17.27%.

(R,S)-2-(2,3-Dihydro-1H-3a,6-diaza-cyclopenta[a]inden-8-yl)-1-methylethylamine dihydrochloride To a solution of 8-(2-nitro-propenyl)-2,3-dihydro-1H-3a,6-diaza-cyclopenta[a]indene (0.200 g 0.82 mMol) in tetrahydrofuran (2 ml) was added dropwise a 1M solution of lithium aluminum hydride (2 ml, 2 mMol)in THF at 0° C. with stirring under argon. The mixture was then heated to reflux for 4 h, was cooled to 0° C. and a 10% solution of sodium-potassium tartrate in water (5 ml) was added with stirring. The mixture was briefly heated to reflux cooled to room temperature and filtered through a pad of dicalite. The clear filtrate was extracted with dichloromethane. The organic phase was dried with sodium sulfate evaporated and the residue was purified by chromatography on silica gel eluting with dichloromethane: methanol: conc. ammonia= 9:1:0.1 to yield the title compound as free base as a yellowish oil (90 mg; 51%). To a solution of this oil (80 mg, 0.37 mMol) in tetrahydrofuran (3 ml) was added dropwise with stirring at room temperature a solution of hydrochloric acid in ether (0.2 ml 5.5 M, 1.1 mMol). The resulting suspension was stirred at room temperature for 30 min and the solid was collected by filtration and dried to constant weight under high vacuum at 40° C. to yield the title compound (100 mg, 93%) as a white powder melting above 280° C. Found C, 51.93; H 6.79; N,13.68%; $C_{13}H_{19}N_3$+0.73 mol water requires C,51.81; H,6.84; N,13.94%.NMR $\delta_H$ (400 MHz DMSO-$d_6$) 1.25(d,J=6.4 Hz,3H); 2.63(m,2H); 3.10(m,4H); 3.50 (m,1H); 4.27(t,J=7 Hz,2H); 7.93(d,J=7 Hz,1H); 8.0(s,broad,3H); 8.39(d,J=7 Hz,1H); 9.30 (s,1H); 15.0(s,1H)ppm.

Example 2

(R,S)-2-(2,3-Dihydro-1H-3a,4-diaza-cyclopenta[a] inden-8-yl)-1-methylethylamine Dihydrochloride

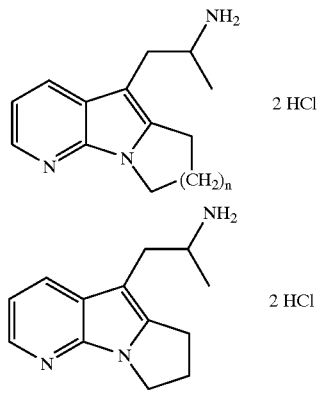

3-(5-Chloropent-1-ynyl)-pyridin-2-ylamine

To a stirred solution of 2-amino-3-iodoaniline (13 g) in triethylamine (260 ml) were added bis(triphenylphosphine) palladium dichloride (2 g) and copper (I) iodide (1.15 g). The mixture was cooled to 5° C. before the addition of 5-chloro-1-pentyne (6.6 ml). The mixture was heated to 50° C. and stirred 5 h. The mixture was cooled to room temperature, filtered and evaporated. The residue was purified by column chromatography on silica gel (ethyl acetate/hexane 1:1 to 5:1 eluant) to afford 3-(5-chloropent-1-ynyl)-pyridin-2-ylamine as a red oil (10.6 g, 92%): MS (EI) 196, 194 (M),159, 157, 131, 104; $^1$H NMR ($\delta$, CDCl$_3$) 8.0 (dd, 1H, J=2,5 Hz), 7.47 (dd, 1H, J=2,7 Hz), 6.59 (dd, 1H, J=5,7 Hz), 4.94 (br s, 1H), 3.72 (t,2H, J=6 Hz), 2.68 (t,2H, J=7 Hz), 2.07 (dt,2H, J=6,7 Hz) ppm.

2-(3-Chloropropyl)-1H-pyrrolo[2,3-b]pyridine 3-(5-Chloropent-1-ynyl)-pyridin-2-ylamine (10.2 g) was dissolved in acetonitrile (120 ml) and the solution cooled to 5° C. under a stream of argon. Trifluoroacetic anhydride (14.1 ml) was added dropwise as a solution in acetonitrile (10 ml). The mixture was stirred 2 h at 0° C. and 10 min at room temperature. The solvent and excess reagent were evaporated under reduced pressure to afford the trifluoroacetate as a viscous oil (20 g) that was used without further purification. The oil was dissolved in acetonitrile (120 ml) and treated with palladium (II) chloride. The mixture was heated under argon 2 h at 75° C., cooled and evaporated under reduced pressure. The residue was taken up in ethyl acetate and the solution washed with 5% aqueous sodium carbonate solution, brine, dried over sodium sulfate and evaporated. The residue was purified by column chromatography on silica gel (ethyl acetate/hexane 1:2 to 1:1 eluant) to afford 2-(3-chloro-propyl)-1 H-pyrrolo[2,3-b] pyridine as a yellow oil (5.6 g, 55%) which solidified on standing. Mp: 75° C.; MS; $^1$H NMR ($\delta$, CDCl$_3$) 11.7 (s,1H), 8.25 (dd,1H, J=1.2,4.8 Hz), 7.86 (dd,1H, J=1.2,8 Hz), 7.06 (dd,1H, J=4.8,8 Hz), 6.25 (s,1H), 3.63 (t,2H, J=6.4 Hz), 3.08 (t,2H, J=7.6 Hz), 2.29 (dt,2H, J=6.4,7.6 Hz) ppm.

2,3-Dihydro-1H-3a,4-diaza-cyclopenta[a]indene 2-(3-Chloro-propyl)-1H-pyrrolo[2,3-b]pyridine (5.6 g) was dissolved in acetonitrile under a stream of argon. Potassium iodide (6 g) was added, and sodium hydride in mineral oil (4.60 g) added in small portions. After stirring 2 h at room temperature, the mixture was poured onto a mixture of ice and saturated sodium hydrogencarbonate solution. The organics were extracted twice with ethyl acetate. The combined organic phases were washed with brine, dried over sodium sulfate and evaporated to afford 2,3-dihydro-1H-3a,4-diaza-cyclopenta[a]indene as a crude pale brown solid (4.5 g, 99%), which was used without further purification. MS (EI) 159 (M+H)$^+$, 143, 100; $^1$H NMR ($\delta$, CDCl$_3$) 8.19 (dd,1H, J=1,5 Hz), 7.80 (dd,1H, J=1,8 Hz), 6.99 (dd,1H, J=5,8 Hz), 6.12 (s,1H), 4.22 (t,2H, J=6 Hz), 3.05 (t,2H, J=8 Hz), 2.63 (dt,2H, J=6,8 Hz) ppm.

2,3-Dihydro-1H-3a,4-diaza-cyclopenta[a]indene-8-carbaldehyde

Phosphorus oxychloride (3.85 ml) was added dropwise to N,N-dimethylformamide (25 ml) cooled in an ice-bath. The mixture was stirred 10 min before the addition of 2,3-dihydro-1H-3a,4-diaza-cyclopenta[a]indene (4.40 g) in N,N-dimethylformamide (7 ml). The mixture was stirred 45 min at 40° C., cooled to room temperature and concentrated aqueous sodium hydroxide added dropwise to pH10. The mixture was heated at 50° C. 10 min, cooled to room temperature and poured onto crushed ice. The organics were extracted with ethyl acetate (2×), the combined organic phases washed with brine, dried over sodium sulfate and evaporated under reduced pressure. The residue was purified by column chromatography on silica gel (ethyl acetate/hexane 1:1 to 1:0) to afford 2,3-dihydro-1H-3a,4-diaza-cyclopenta[a]indene-8-carbaldehyde (2.4 g, 46%) as a light orange oil which solidified on standing. Mp. 137–141; MS (EI): 187 (M+H)$^+$, 143, 100; $^1$H NMR ($\delta$, CDCl$_3$) 10.01 (s, 1H), 8.45 (dd, 1H, J=1,8 Hz), 8.32 (dd, 1H, J=1,5 Hz), 7.23 (dd, 1H, J=5,8 Hz), 4.31 (t, 2H, J=6 Hz), 3.38 (t, 2H, J=8 Hz), 2.76 (dt, 2H, J=6,8 Hz) ppm.

8-(2-Nitropropenyl)-2,3-dihydro-1H-3a,4-diaza-cyclopenta[a]indene

A stirred solution of 2,3-dihydro-1H-3a,4-diaza-cyclopenta[a]indene-8-carbaldehyde (2.3 g) and ammonium acetate (1.05 g) in nitroethane was heated to 100° C. for 2.5 h, cooled to room temperature, and evaporated under reduced pressure. The residue was partitioned between water and ethyl acetate, the phases separated, the aqueous phase re-extracted with ethyl acetate. The combined organic phases were dried over sodium sulfate and evaporated under reduced pressure. The residue was purified by column chromatography on silica gel (ethyl acetate/hexane 2:1 to 4:1) to afford 8-(2-nitropropenyl)-2,3-dihydro-1H-3a,4-diaza-cyclopenta[a]indene as a yellow solid (2.4 g, 80%); MS (EI) 244 (M+H)$^+$, 224, 195, 171; $^1$H NMR ($\delta$, CDCl$_3$) 8.31 (dd, 1H, J=1,5 Hz), 8.29 (s, 1H), 7.92 (dd, 1H, J=1,8 Hz), 7.16 (dd,1H, J=5,8 Hz), 4.34 (t,2H, J=6 Hz), 3.18 (t,2H, J=8 Hz), 2.72 (dt,2H, J=6,8 Hz), 2.45 (s,3H) ppm.

(R,S)-2-(2,3-Dihydro-1H-3a,4-diaza-cyclopenta[a]inden-8-yl)-1-methylethylamine Dihydrochloride To lithium aluminium hydride (30 mg) in tetrahydrofuran (1 ml) at room temperature was slowly added a solution of 8-(2-nitropropenyl)-2,3-dihydro-1H-3a,4-diaza-cyclopenta[a]indene (98 mg) in tetrahydrofuran (1 ml). The mixture was heated at reflux for 3 h, cooled to room temperature and 1M aqueous sodium hydroxide solution added dropwise. The mixture was stirred 30 min, and poured into ethyl acetate. The phases were separated, the aqueous phase re-extracted with ethyl acetate. The combined organic phases were washed with brine, dried over sodium sulfate and evaporated under reduced pressure. The residue was purified by column chromatography on silica gel (dichloromethane/methanol/ammonia 9:1:0.1) to afford (R,S)-2-(2,3-dihydro-1H-3a,4-diaza-cyclopenta[a]inden-8-yl)-1-methyl-ethylamine. This was treated with a solution of hydrochloric acid in ether. The mixture was stirred 15 min at room temperature and the solvent evaporated under reduced pressure. The residue was recrystallised from ethanol/ether to afford (R,S)-2-(2,3-dihydro-1H-3a,4-diaza-cyclopenta[a]inden-8-yl)-1-methylethylamine dihydrochloride as a white solid (18 mg); MS (EI): 216 (M+H)+, 143, 117, 100; $^1$H NMR (δ, d6-DMSO) 8.42 (d, 1H, J=8 Hz), 8.3 (d, 1H, J=5 Hz), 8.15 (br s, 2H), 7.35 (dd, 1H, J=5,8 Hz), 5.1 (br s, 4H), 4.25 (t, 2H, J=5 Hz), 3.4 (m, 1H), 3.05 (m, 2H), 2.95 (m,1H), 2.58 (t, 2H, J=6 Hz), 1.24 (d, 3H, J=6 Hz) ppm.

Example 3

(S)-2-(2,3-Dihydro-1H-3a,5-diaza-cyclopenta[a]inden-8-yl)-1-methylethylamine

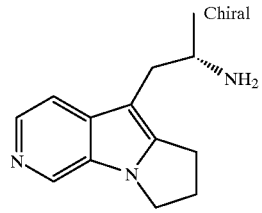

2,3-Dihydro-1H-3a,5-diaza-cyclopenta[a]indene

A mixture of 0.2885 g bis(triphenylphosphine) palladium dichloride and 0.1565 g copper (I) iodide in 200 mL triethylamine was heated to reflux for 20 min. To the resulting solution was added at room temperature 25.00 g N-(4-iodo-3-pyridinyl)-2,2-dimethyl-propanamide and 25.3 g 5-chloro-1-pentyne and the mixture was heated to reflux for 30 min. The reaction mixture was distributed between water and ethyl acetate, the phases were separated and the organic phase was washed with water and brine, dried over magnesium sulfate and evaporated. The residue was taken up in 200 mL tert-butanol and 18.45 g powdered potassium hydroxyde was added. The mixture was heated to reflux for 30 min. The reaction mixture was distributed between water and ethyl acetate, the phases were separated and the organic phase was washed with water and brine, dried over magnesium sulfate and evaporated. The residue was purified by chromatography on silica gel with ethyl acetate:methanol= 7:3 to yield 7.37 g 2,3-Dihydro-1H-3a,5-diaza-cyclopenta[a]indene as slightly yellow solid melting at 90–91° C.

8-Bromo-2,3-dihydro-1H-3a,5-diaza-cyclopenta[a]indene

To a solution of 1.58 g in 15 ml dimethylformamide is added dropwise 20 ml of a 10% solution of bromine in dimethylformamide. The mixture was stirred at room temperature for 45 min. The reaction mixture was distributed between water and ethyl acetate, the phases were separated and the organic phase was washed with water and brine, dried over magnesium sulfate and evaporated. The residue was purified by chromatography on silica gel with ethyl acetate:methanol=9:1 and recrystallized from cyclohexane to yield 1.338 g 8-bromo-2,3-dihydro-1H-3a,5-diaza-cyclopenta[a]indene as off white crystals melting at 110.8–112° C.

c) (S)-2-(2,3-Dihydro-1H-3a,5-diaza-cyclopenta[a]inden-8-yl)-1-methyl-ethylamine To a solution of 0.237 g 8-bromo-2,3-dihydro-1H-3a,5-diaza-cyclopenta[a]indene in 3 ml tetrahydrofuran was added dropwise a 1.6M solution of n-butyl lithium in n-hexane during 15 min at −78° C. The mixture was stirred at −78° C. for 30 min. To the resulting mixture was added (S)-4-Methyl-2,2-dioxo-[1,2,3]oxathiazolidine-3-carboxylic acid tert-butyl ester at once. The mixture was allowed to warm to room temperature during 15 min. The reaction mixture was distributed between water and ethyl acetate, the phases were separated and the organic phase was washed with water and brine, dried over magnesium sulfate and evaporated. The residue was dissolved in 5 mL trifluoro acetic acid and kept at room temperature for 10 min. The solvent was evaporated and the residue was purified by chromatography on silica gel with dichloromethane:methanol:ammonia=9:1:01 to yield 0.045 g (S)-2-(2,3-Dihydro-1H-3a,5-diaza-cyclopenta[a]inden-8-yl)-1-methyl-ethylamine as a white solid.

MS: 216.4 d) (S)-4-Methyl-2,2-dioxo-[1,2,3]oxathiazolidine-3-carboxylic acid tert-butyl ester By the same general procedure as in Example 7b (S)-4-Methyl-2,2-dioxo-[1,2,3]oxathiazolidine-3-carboxylic acid tert-butyl ester was obtained from (S)-BOC-alalinol as white crystals melting at 121.1–121.8° C. after crystallisation from tert. butylmethlyether.

Example 4

(R)-2-(2,3-Dihydro-1H-3a,5-diaza-cyclopenta[a]inden-8-yl)-1-methyl-ethylamine a) (R)-2-(2,3-Dihydro-1H-3a,5-diaza-cyclopenta[a]inden-8-yl)-1-methyl-ethylamine

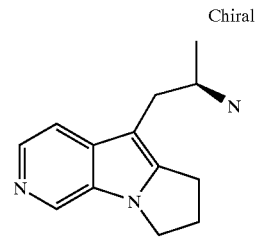

By exactly the same procedure as in 3b the enantiomer (R)-2-(2,3-Dihydro-1 H-3a,5-diaza-cyclopenta[a]inden-8-yl)-1-methyl-ethylamine was obtained from 8-bromo-2,3-dihydro-1H-3a,5-diaza-cyclopenta[a]indene in 3 ml tetrahydrofuran by using the R-enantiomeric sulfamidate (R)-4-Methyl-2,2-dioxo-[1,2,3]oxathiazolidine-3-carboxylic acid tert-butyl ester.

MS: 216.4 b) (R)-4-Methyl-2,2-dioxo-216-[1,2,3]oxathiazolidine-3-carboxylic acid tert-butyl ester By the same general procedure as in Example 7b (R)-4-Methyl-2,2-dioxo-[1,2,3]oxathiazolidine-3-carboxylic acid tert-butyl ester was obtained from (R)-BOC-alalinol as white crystals melting at 118.5–119.1° C. after crystallisation from tert. butylmethlyether.

Example 5

(S)-2-(2,3-Dihydro-1H-3a,6-diaza-cyclopenta[a]inden-8-yl)-1-methyl-ethylamine

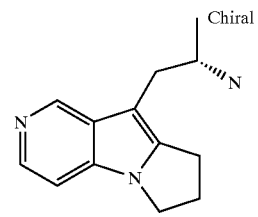

By the same general procedures as in example 3 (S)-2-(2,3-Dihydro-1H-3a,6-diaza-cyclopenta[a]inden-8-yl)-1- methyl-ethylamine was obtained from 8-Bromo-2,3-dihydro-1H-3a,6-diaza-cyclopenta[a]indene (MS: 238, 238) and (S)-4-Methyl-2,2-dioxo-[1,2,3]oxathiazolidine-3-carboxylic acid tert-butyl ester as white solid.

MS: 216.3

Example 6

(R)-2-(2,3-Dihydro-1H-3a,6-diaza-cyclopenta[a]inden-8-yl)-1-methyl-ethylamine

Chiral

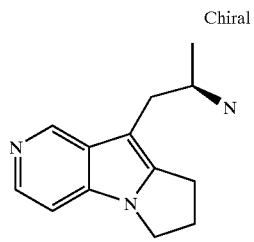

By the same general procedure as in example 3(R)-2-(2,3-Dihydro-1H-3a,6-diaza-cyclopenta[a]inden-8-yl)-1-methyl-ethylamine was obtained from 8-Bromo-2,3-dihydro-1H-3a,6-diaza-cyclopenta[a]indene and (R)-4-Methyl-2,2-dioxo-[1,2,3]oxathiazolidine-3-carboxylic acid tert-butyl ester as white solid.

MS: 216.3

The products from examples 5 and 6 were both shown to be enantiomerically pure (>98%ee) by chiral GC on a BGB-175 column.

Example 7

2-(2,3-dihydro-1H-3a,6-diaza-cyclopenta[a]inden-8-yl)-ethylamine

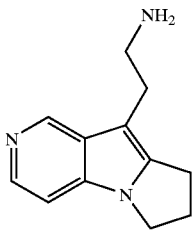

7a) By the same general procedure as in example 3 there was obtained from 8-Bromo-2,3-dihydro-1H-3a,6-diaza-cyclopenta[a]indene and 2,2-dioxo-[1,2,3]oxathiazolidine-3-carboxylic acid tert-butyl ester after protecting group cleavage 2-(2,3-dihydro-1H-3a,6-diaza-cyclopenta[a]inden-8-yl)-ethylamine as white solid.

MS: 201.2

7b) 2,2-Dioxo-[1,2,3]oxathiazolidine-3-carboxylic acid tert-butyl ester To a solution of 3.22 g BOC-glycinol in 30 ml tetrahydrofuran was added at −78° C. 25 ml of a ca 1.6 M solution of n-butyllithium in n-hexane with stirring. The temperature rose to −45° C. The cooling bath was removed and the temperature was allowed to rise to 0° C. during 30 min. The mixture was then cooled to −78° C. and a solution of 2,376 g thionylchloride in 15 ml THF which was cooled to −78° C. in a jacketed dropping funnel was added at once with vigorous stirring. The temperature rose to ca −50° C. The cooling bath was replaced by an ice bath and the mixture was allowed to stir at 0° C. for 30 min. The reaction mixture was distributed between water and ethyl aceate. The phases were separated and the organic phase was washed with 10% citric acid,10% sodium bicarbonate and brine, dried over magnesiumsulfate and purified by chromatography on silica gel with hexane:ethyl acetate=1:1 to yield 2.00 g of the sulfamidite inermediate as white crystals. To a solution of 1,75 g of this material in 20 ml ethyl acetate was added at 0° C. 25 mL of a 10% solution of sodiummetaperiodate in water. To the well stirred mixture was added 24 mg rutheniumdioxide hydrate. The mixture was stirred at 0° C. for 30 min. The phases were separated and ca 2 mL isopranol was added to the organic phase. The organic phase was washed with 10% citric acid, 10% sodium bicarbonate and brine, dried with magnesium sulfate and evaporated to dryness. The solid product was recrystallized from t-butylmethylether to yield 1.24 g 2,2-dioxo-[1,2,3]oxathiazolidine-3-carboxylic acid tert-butyl ester as white crystals melting at 121.6–122.1° C.

What is claimed is:

1. An aza-indolyl derivative selected from the group consisting of a compound of formula (I):

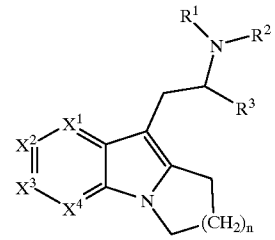

(I)

wherein n is 1,2 or 3;

$X^1$ is nitrogen or $CR^4$; $X^2$ is nitrogen or $CR^5$; $X^3$ is nitrogen or $CR^6$; $X^4$ is nitrogen or $CR^7$;

wherein one or two of $X^1$, $X^2$, $X^3$ and $X^4$ are nitrogen;

$R^1$, $R^2$ and $R^3$ are independently selected from hydrogen and alkyl;

$R^4$, $R^5$, $R^6$ and $R^7$ are independently selected from hydrogen, halogen, hydroxy, alkyl, aryl, alkoxy, aryloxy, alkylthio, arylthio, alkylsulfonyl, alkylsulfoxyl, arylsulfonyl, arylsulfoxyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, and wherein for each of $X^1$, $X^2$, $X^3$ and $X^4$ which is nitrogen, adjacent ring atoms selected from the group consisting of $X^1$, $X^2$, $X^3$ and $X^4$ are not substituted by halogen;

and pharmaceutically acceptable salts thereof.

2. The aza-indolyl derivative of claim 1, wherein the compound of formula (I) is in the form of the enantiomer shown in formula (Ia):

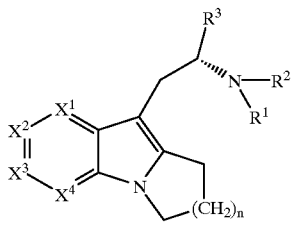

(Ia)

wherein $R^1$, $R^2$, $R^3$, $X^1$, $X^2$, $X^3$, $X^4$ and n are defined as in claim 1.

3. The aza-indolyl derivative of claim 1, wherein two of $X^1$, $X^2$, $X^3$ and $X^4$ are nitrogen and these nitrogen atoms are in meta or para position to each other.

4. The aza-indolyl derivative of claim 1, wherein $X^1$ is nitrogen, $X^2CR^5$, $X^3$ is $CR^6$, and $X^4$ is $CR^7$.

5. The aza-indolyl derivative of claim 1, wherein $X^1$ is $CR^4$; $X^2$ is nitrogen; $X^3$ is $CR^6$ and $X^4$ is $CR^7$.

6. The aza-indolyl derivative of claim 1, wherein $X^1$ is $CR^4$, $X^2$ is $CR^5$; $X^3$ is nitrogen and $X^4$ is $CR^7$.

7. The aza-indolyl derivative of claim 1, wherein $X^1$ is $CR^4$; $X^2$ is $CR^5$; $X^3$ is $CR^6$ and $X^4$ is nitrogen.

8. The aza-indolyl derivative of claim 1, wherein $X^1$ is nitrogen, $X^2$ is $CR^5$; $X^3$ is nitrogen and $X^4$ is $CR^7$.

9. The aza-indolyl derivative of claim 1, wherein $X^1$ is $CR^4$, $X^2$ is nitrogen, $X^3$ is $CR^6$ and $X^4$ is nitrogen.

10. The aza-indolyl derivative of claim 1, wherein $X^1$ is nitrogen, $X^2$ is $CR^5$, $X^3$ is $CR^6$ and $X^4$ is nitrogen.

11. The aza-indolyl derivative of claim 1, wherein n is 1.

12. The aza-indolyl derivative of claim 1, wherein $R^1$ and $R^2$ are hydrogen.

13. The aza-indolyl derivative of claim 1, wherein $R^1$ is hydrogen and $R^2$ is alkyl.

14. The aza-indolyl derivative of claim 1, wherein $R^1$ is hydrogen and $R^2$ is arylalkyl.

15. The aza-indolyl derivative of claim 1, wherein $R^3$ is methyl.

16. The aza-indolyl derivative of claim 1, wherein $R^3$ is hydrogen.

17. The aza-indolyl derivative of claim 1, wherein $R^4$, $R^5$, $R^6$ and $R^7$ are selected from hydrogen, halogen, hydroxy, alkyl, aryl, alkoxy, aryloxy, alkylthio, alkylsulfoxyl and alkylsulfonyl.

18. The aza-indolyl derivative of claim 1, wherein $R^4$ is hydrogen or halogen.

19. The aza-indolyl derivative of claim 1, wherein $R^5$ is not hydrogen.

20. The aza-indolyl derivative of claim 19, wherein $R^5$ is selected from halogen, alkyl, alkoxy and alkylthio.

21. The aza-indolyl derivative of claim 1, wherein $R^6$ is not hydrogen.

22. The aza-indolyl derivative of claim 1, wherein $R^6$ is selected from hydrogen and halogen.

23. The aza-indolyl derivative of claim 1, wherein two or three of $R^4$, $R^5$, $R^6$ and $R^7$ are hydrogen.

24. The aza-indolyl derivative of claim 1, wherein n is 1 or 2;

one of $X^1$, $X^2$, $X^3$ and $X^4$ is nitrogen and the remainder is CH; and $R^1$, $R^2$ and $R^3$ are independently selected from hydrogen and lower alkyl.

25. The aza-indolyl derivative of claim 24, wherein said compound of formula (I) is (S)-2-(2,3-dihydro-1H-3a,5-diaza-cyclopenta[a]inden-8-yl)-1-methyl-ethylamine.

26. The aza-indolyl derivative of claim 24, wherein said compound of formula (I) is (R)-2-(2,3-dihydro-1H-3a,5-diaza-cyclopenta[a]inden-8-yl)-1-methyl-ethylamine.

27. The aza-indolyl derivative of claim 24, wherein said compound of formula (I) is (S)-2-(2,3-dihydro-1H-3a,6-diaza-cyclopenta[a]inden-8-yl)-1-methyl-ethylamine.

28. The aza-indolyl derivative of claim 24, wherein said compound of formula (I) is (R)-2-(2,3-dihydro-1H-3a,6-diaza-cyclopenta[a]inden-8-yl)-1-methyl-ethylamine.

29. The aza-indolyl derivative of claim 24, wherein said compound of formula (I) is (R)-2-(2,3-dihydro-1H-3a,4-diaza-cyclopenta[a]inden-8-yl)-1-methyl-ethylamine.

30. The aza-indolyl derivative of claim 24, wherein said compound of formula (I) is (S)-2-(2,3-dihydro-1H-3a,4-diaza-cyclopenta[a]inden-8-yl)-1-methyl-ethylamine.

31. The aza-indolyl derivative of claim 24, wherein said compound of formula (I) is 2-(2,3-dihydro-1H-3a,6-diaza-cyclopenta[a]inden-8-yl)-ethylamine.

* * * * *

UNITED STATES PATENT AND TRADEMARK OFFICE
CERTIFICATE OF CORRECTION

PATENT NO. : 6,583,134 B2
DATED : June 24, 2003
INVENTOR(S) : Jonathan Mark Bentley, Paul Ebeisen and Sven Taylor It is certified that error appears in the above-identified patent and that said Letters Patent is hereby corrected as shown below:

Column 23,
Line 19, "$X^2CR^5$" should read -- $X^2$ is $CR^5$ --

Signed and Sealed this

Second Day of December, 2003

JAMES E. ROGAN
*Director of the United States Patent and Trademark Office*